United States Patent
Lazarus (12) 
(10) Patent No.: US 6,235,286 B1
(45) Date of Patent: *May 22, 2001

(54) ADULT-ONSET DIABETES TREATMENT METHOD

(76) Inventor: Douglas D. Lazarus, 17 Winter St., Apt. 17, Watertown, MA (US) 02472

(*) Notice: Subject to any disclaimer, the term of this patent is extended or adjusted under 35 U.S.C. 154(b) by 0 days.

This patent is subject to a terminal disclaimer.

(21) Appl. No.: 09/218,198

(22) Filed: Dec. 22, 1998

Related U.S. Application Data (63) Continuation-in-part of application No. 08/799,094, filed on Feb. 11, 1997, now Pat. No. 5,851,531.
(60) Provisional application No. 60/017,179, filed on May 9, 1996.

(51) Int. Cl.[7] .................................................. A61K 35/78
(52) U.S. Cl. .......................................................... 424/195.1
(58) Field of Search ........................................ 424/195.1

(56) References Cited

U.S. PATENT DOCUMENTS

| | | | |
|---|---|---|---|
| 4,985,248 | 1/1991 | Liu | 424/195.1 |
| 5,851,531 | * 12/1998 | Lazarus | 424/195.1 |

FOREIGN PATENT DOCUMENTS 08157495   6/1996   (JP).

OTHER PUBLICATIONS

Sigma Catalog (1993) p. 126.
Newsholme et al., *Biochemistry for the Medical Science*, (1983), John Wiley: London, p. 706.
Akhtar, "Trial of Momordica Charantia Linn (Karela) Powder in Patients with Maturity–Onset Diabetes", *J. Pakistan Medical Assn.*, 32(4), (1982), 106–7.
Waxdal, M., "Isolation, Characterization and Biological Activities of Five Mitogens from Pokeweed", *Biochemistry 13(18)*, (1974) 3671–77.
Ng et al., "Isolation and Characterization of a Galactose Binding Lectin with Insulinomimetic Activities", *Int. J. Peptide Res.*, 28, (1986) 163–172.
Bardocz et al., *British Journal of Nutrition*, 76, (1996) 613–626.

* cited by examiner

*Primary Examiner*—Jean C. Witz
(74) *Attorney, Agent, or Firm*—Synnestvedt & Lechner LLP (57) ABSTRACT

Methods of inducing weight loss and treating adult-onset diabetes in a mammal in need thereof by administering to the mammal Momordica lectin or pokeweed mitogen chloroform precipitatable fraction. Lectin pharmaceutical compositions are also disclosed.

23 Claims, 3 Drawing Sheets

ADULT-ONSET DIABETES TREATMENT METHOD

CROSS-REFERENCE TO RELATED APPLICATION

This application is a Continuation-in-Part of U.S. patent application Ser. No. 08/799,094 filed Feb. 11, 1997, which issued as U.S. Pat. No. 5,851,531 on even date herewith, Dec. 22, 1998, and in turn claims priority benefit of U.S. Provisional Application No. 60/017,179, filed May 9,1996. The disclosure of U.S. Pat. No. 5,851,531 is incorporated herein by reference.

BACKGROUND OF THE INVENTION

The present invention relates to methods of treating adult onset diabetes by administering to a patient in need thereof an effective amount of a lectin capable of inducing a decline in food intake and inducing hypoglycemia. The present invention also relates to methods of inducing weight loss by administering an effective amount of a lectin capable of inducing a decline in food intake and repeating the administering step to maintain the decline in food intake. In particular, the present invention relates to methods of treating adult-onset diabetes and inducing weight loss with the mixture of lectins known as pokeweed mitogen and the bitter pear melon lectin.

Adult-onset Type II diabetes mellitus is a major health problem in this country. Because it is exacerbated by obesity, treatment of this disease is often two-pronged, using drugs to maintain normal blood glucose concentrations and diet therapy to promote weight loss. However, current hypoglycemia drugs are not always effective, and adherence to diet therapy is generally poor.

Lectins are a general class of proteins that bind to carbohydrates. The binding of these lectins to carbohydrates that are part of cell membrane receptors can result in cell activation. This is particularly well characterized with cells of the immune system. Lectins are widely used to stimulate immune function in in vitro studies.

The crude extract of the lectins from the pokeweed plant, *Phytolacca americana* is referred to as pokeweed mitogen. Pokeweed mitogen is a mixture of five lectins, which are designated as Pa-1 to Pa-S. These range in size from 19 to 30 kD, and contain approximately 3 percent carbohydrate. The ligand for all the pokeweed lectins is N-acetyl glucosamine. Despite binding to the same ligands, there is a disparity between the bioactivity of the five pokeweed mitogen lectins. Only Pa-1 is a polymer, and only Pa-1 stimulates B cells. Further, Pa-2 to Pa-5, all of which stimulate T cells, do so with widely differing potency.

Effects attributed to pokeweed mitogen include stimulation of the immune system, with the appearance of plasma cells in the peripheral circulation, the release of interferon-y and tryptophan metabolites, and transient splenomegaly secondary to blood engorgement. Zazula et al., *P.S.E.B.M.*, 133, 1088–92 (1970), disclosed that the intravenous injection of pokeweed mitogen to mice produced a marked increase in the weight of the spleen, with an increase in the number of nucleated cells, lymphoblasts, and mitotic figures. A marked increase in the total number of plasma cells was also produced, but these cells did not appear in the peripheral blood, and the effect of pokeweed mitogen was limited to a transient leukopenia. One to three days after the administration of pokeweed mitogen at a level of 175 mg/kg, all mice lost an average of 1.5 g of body weight, but by day five showed a net weight gain. Weight loss following pokeweed mitogen infusion is not consistently reported in the literature.

Wheat germ agglutinin is a lectin that shares structural and binding properties with pokeweed mitogen lectins. Mice given wheat germ agglutinin developed a non-significant hypoglycemia and a decline in food intake, but no weight loss. Like Pa-2 to Pa-5, wheat germ agglutinin stimulates T cells.

There exists a need for a pharmaceutical composition for the treatment of diabetes mellitus that produces both a lowered circulating glucose level and an anorexic state that results in the loss of body weight.

SUMMARY OF THE INVENTION

This need is met by the present invention. It has now been discovered that a chloroform precipitatable fraction of pokeweed mitogen likely to be lectin Pa-1 not only possesses the insulinomimetic properties of wheat germ agglutinin, thereby producing a decline in circulating glucose levels by binding to cell insulin receptors, but, unlike wheat germ agglutinin, Pa-1 also binds to insulin receptors in the brain to produce an anorexic state and consequent weight loss. It has further been discovered that the lectin from the bitter pear melon *Momordica charantia* also induces hypoglycemia and an anorexic state and consequential weight loss to a degree equivalent to that induced by the Pa-1 chloroform precipitate.

Therefore, according to one aspect of the present invention, there is provided a method of treating adult-onset diabetes in a mammal in need thereof by administering to the mammal a pokeweed mitogen chloroform precipitatable fraction in an amount between about 1 and about 100 micrograms per kilogram of body weight that is effective to induce hypoglycemia in said mammal.

According to another aspect of the present invention there is provided a method of treating adult-onset diabetes in a mammal in need thereof by administering to the mammal a dosage form consisting essentially of Momordica lectin in an amount effective to induce hypoglycemia in the mammal. Preferred methods in accordance with this aspect of the present invention further include the step of continuing the administering step to maintain the hypoglycemia state. The preferred dosage amount is between about 1 and about 100 micrograms per kg of body weight per day, and even more preferable is an amount effective to induce a decline in food intake. An even more preferred method continues the administering step daily until the decline in food intake produces a weight loss of at least about 10 percent.

The lectins of the present invention also induce a decline in food intake and consequential weight loss and may be administered advantageously to any patient who would obtain a health benefit from a loss of weight. Therefore, according to another aspect of the present invention, there is provided a method of inducing weight loss in a mammal in need thereof by administering to the mammal a lectin selected from a pokeweed mitogen chloroform precipitatable fraction and Momordica lectin in an amount between about 1 and about 100 micrograms per kg. of body weight per day that is effective to stimulate a decline in food intake in the mammal, and continuing the administering step to maintain the decline in food intake.

The present invention incorporates the discovery that the lectins of the present invention may be administered in an amount that stimulates a decline in food intake without inducing hypoglycemia. Therefore, preferred weight loss methods according to the present invention administer to the mammal a pokeweed mitogen chloroform precipitatable fraction or Momordica lectin in an amount effective to induce a decline in food intake in the mammal without inducing hypoglycemia.

However, dosage levels that induce both a decline in food intake and hypoglycemia may be advantageously employed in the treatment of adult-onset diabetes to control both blood sugar levels and patient weight. Therefore, according to another aspect of the present invention, there is provided a method of treating adult-onset diabetes in a mammal in need thereof by administering to the mammal a dosage form consisting essentially of Momordica lectin in an amount effective to induce a decline in food intake and induce hypoglycemia in the mammal, and repeating the administering step daily until the decline in food intake produces a weight loss of at least about 10%.

The present invention also includes pharmaceutical compositions consisting essentially of an effective amount of lectin selected from pokeweed mitogen chloroform precipitatable fraction and Momordica lectin, and a pharmaceutically acceptable carrier. The pharmaceutical compositions of the present invention may be in either oral or systemic dosage forms.

While not being bound by any particular theory, it is believed that pokeweed mitogen chloroform precipitatable fraction and Momordica lectin produced weight loss in addition to hypoglycemia by crossing the blood-brain barrier and binding to insulin receptors in the brain. It is believed that other lectins that produced only hypoglycemia without a corresponding weight loss are capable of binding to cell membrane insulin receptors to increase cellular glucose uptake and reduce circulating glucose levels, but are incapable of crossing the blood-brain barrier to bind to insulin receptors in the brain.

While weight loss following pokeweed mitogen infusion was not consistently shown in the prior art literature, the contradictory findings are believed to have resulted from differing preparations of the pokeweed mitogen, with the predominance of different forms of the lectins. The present invention incorporates the discovery that in order to obtain consistent weight loss, a pokeweed mitogen chloroform precipitatable fraction must be employed.

The above and other objects, features and advantages of the present invention will become clear from the following description of the preferred embodiments considered in conjunction with the accompanying drawings.

BRIEF DESCRIPTION OF THE DRAWINGS

FIG. 1*a* depicts the effect of pokeweed mitogen on circulating glucose and lactate in mice;

FIG. 1*b* depicts the effect of pokeweed mitogen on circulating insulin in mice;

FIG. 2*a* depicts the effect of pokeweed mitogen on circulating glucose and food intake in mice;

FIG. 2*b* depicts the effect of pokeweed mitogen on body, carcass and epididymal fat pad weight in mice;

FIG. 3*a* depicts the effect of pokeweed mitogen on body weight in mice; and FIG. 3*b* depicts the effect of pokeweed mitogen on food intake in mice.

DETAILED DESCRIPTION OF THE PREFERRED EMBODIMENT

It has surprisingly been discovered that mice given the lectins pokeweed mitogen chloroform precipitatable fraction and Momordica lectin exhibited a significant decline in circulating glucose levels that was not secondary to the decline in food intake that also developed, or to changes in insulin secretion produced by the lectin. Furthermore, the decline in food intake which developed alone was not sufficient to cause the rapid weight loss that resulted in mice given the pokeweed mitogen and Momordica lectins. Instead, this was the combined result of the decline in food intake and concomitant hypoglycemia.

Essentially any lectin capable of inducing both hypoglycemia and a decline in food intake is suitable for use in the present invention. Suitable lectins may be identified by administering candidate lectins to laboratory test animals and then observing the test animals for an induced lowering of serum glucose levels by a statistically significant degree accompanied by a statistically significant weight loss.

Examples of lectins suitable for use with the present invention include, but are not limited to, the pokeweed mitogen chloroform precipitatable fraction and the Momordica lectin. The chloroform precipitatable pokeweed mitogen fraction can be administered in the form of pokeweed mitogen containing other fractions, provided that the chloroform precipitatable fraction is present. It is preferred, however, that the chloroform precipitatable fraction be administered essentially free of lectins Pa-2 to Pa-4. Unlike other components of pokeweed, the lectins are not toxic.

The term "pokeweed mitogen" as used herein refers to the mixture of five lectins obtained from the plant *Phytolacca americana*. Specific pokeweed mitogen lectins are individually referred to as Pa-1, Pa-2, Pa-3, and the like. When administered as a mixture of the five lectins, either orally or by intra peritoneal injection, pokeweed mitogen induced hypoglycemia, a decline in food intake, and concomitant weight loss, in normal mice, diabetic mice, mice without T or B lymphocytes, and obese mice.

According to this invention, in the treatment of adult onset diabetes, mammals are administered an effective amount of a lectin capable of stimulating a decline in food intake and inducing hypoglycemia. From about 1.0 to about 5.0 mg of lectin per kilogram of body weight will produce the desired result; however, from about 1 to about 100 micrograms of lectin per kilogram of body weight per day is preferably administered, and from about 25 to about 75 micrograms of lectin per kilogram of body weight per day is more preferably administered.

To induce weight loss, mammals are administered an effective amount of a lectin capable of inducing a decline in food intake. From about 0.25 to about 3.0 mg of lectin per kilogram of body weight is effective; however a dosage amount 1 and about 100 micrograms per kilogram of body weight per day is preferred. Again, the lectin should be administered daily at the beginning to maintain the decline in food intake. Most preferably, the mammal should be administered an amount of lectin effective to induce a decline in food intake without inducing hypoglycemia. Typically, this is between about 25 to about 100 micrograms of lectin per kilogram of body weight per day.

The amount, frequency and period of lectin administration will vary depending upon factors such as the level of circulating blood glucose and the weight of the patient. Usually, the administration of the lectin will be daily initially and then less frequently once the desired glucose level and body weight is obtained. Daily dosages may be given by repeatedly administering a unit dosage form. In the alternative, a continuous dosage form such as a timed-release tablet or capsule or a transdermal drug delivery device may be employed to continuously administer the lectin.

To induce weight loss, the lectin should be administered daily until a weight loss of at least 10 percent, and preferably at least 20 percent, if attained, after which the dosage amount may be reduced or administered less frequently. In treatment of adult-onset diabetes, the lectin should be administered daily until the circulating blood glucose level drops below about 150 mg/dl, and preferably below about 120 mg/dl, or until a weight loss of at least about 10 percent, and preferably about 20 percent is obtained, after which the lectin dosage may be reduced or administered less frequently. Preferably, the lectin dosage is not reduced or administered less frequently until both a reduction in circulating blood glucose level below about 150 mg/dl and a loss of body weight of at least about 10 percent is obtained. Precise dosage amounts and frequency, and subsequent changes thereof, may be determined during initial and subsequent screenings of circulating glucose levels and body weight, and is well within the ability level of the ordinarily skilled medical practitioner.

The role of the triterpene compounds found in pokeweed in inducing hypoglycemia and weight loss has been ruled out. More particularly, the triterpenes contained in ginseng stimulate glucose uptake in sheep red blood cells. Although this effect could have accounted for the hypoglycemia and weight loss that developed after pokeweed mitogen was given to mice, the decline in glucose was unaffected when pokeweed mitogen was added to blood. Further, a substance extracted from a pokeweed mitogen preparation by chloroform caused hyperglycemia, rather than hypoglycemia. It is believed that the triterpenes present in pokeweed may have binding properties similar to that of ginseng, but are antagonists rather than agonists. That is, they block the activity that ginseng-derived triterpenes stimulate.

A role for the T or B lymphocytes induced by pokeweed mitogen in inducing hypoglycemia and weight loss has also been ruled out by the use of Severe Combined Immuno Deficiency (SCID) mice. These animals lack functional T and B lympho-cytes, but responded with hypoglycemia and weight loss anyway, and also exhibited an increase in circulating IL-6. Blood IL-6 concentrations declined in mice given the TNF-α antagonist, suggesting that TNF-α synthesis was stimulated by pokeweed mitogen, though secretion was not. Circulating TNF-α was undetectable. The persistence of an IL-6 response despite blockade of TNF-α suggested that pokeweed mitogen induced the direct release of this cytokine. IL-6 is a mediator of hypoglycemia, and is believed to be contributor to the changes induced by pokeweed mitogen.

The hypoglycemia following lectin administration was shown not to be secondary to an increase in circulating insulin. In fact, serum concentrations of insulin declined after pokeweed mitogen was given. Mice made diabetic by treating with streptozotocin also had lower glucose concentrations following pokeweed mitogen treatment, further ruling out the involvement of insulin. Because neither a wholly cytokine-mediated effect nor insulin involvement in the decline in circulating glucose could be demonstrated, the direct effect of pokeweed mitogen was indicated. Elevated deoxyglucose uptake by C2C12 myotubes exposed to a Pa-1 enriched fraction of pokeweed mitogen suggests a direct mechanism for the hypoglycemia induced by pokeweed mitogen. Because insulin induced a decline in food intake and body weight when it was infused into the brain, a direct mechanism is also indicated for the weight loss induced by pokeweed mitogen. The decline in body weight obtained following pokeweed mitogen administration was found to be due to a loss of both protein and fat stores. The combination of a decline in food intake and hypoglycemia is thus believed to promote exaggerated mechanisms of adaptation to starvation, such as elevated mobilization of energy from muscle and fat depots.

Potential toxicity of pokeweed mitogen as the cause of the metabolic changes has been ruled out. Lectins from pokeweed have been shown to be non-toxic when given to mice and after ingestion by humans. Kidney, liver and lung function are not affected by pokeweed mitogen. Studies of the central nervous and cardiovascular systems in animals and humans exposed to pokeweed mitogen have also found no deleterious effects. Mortality resulting from higher chronic doses given to laboratory animals in studies in accordance with the present invention was believed to be secondary to starvation.

Administration of the dose can be oral, intravenous, parenteral, subcutaneous, intramuscular, transdermal, or by any other acceptable method. The lectins can be administered in any number of conventional dosage forms. Oral preparations may be in the form of tablets or capsules prepared using appropriate binders and excipients. Intravenous, parenteral, subcutaneous and intramuscular preparations include sterile solutions or suspensions. Continuous dosage forms such as sustained release oral preparations and devices for transdermal delivery are also contemplated. The solutions to be administered may be reconstituted lyophilized powders and they may additionally contain preservatives, buffers, dispersants, and the like. The pharmaceutical compositions contemplated by the above dosage forms can be prepared with conventional pharmaceutically acceptable ingredients, using conventional formulations and techniques.

Preferably, the lectin is administered either orally or, in the alternative, systemically via subcutaneous or intramuscular injection or by transdermal delivery. When administered orally to mice, pokeweed mitogen induced hypoglycemia, a decline in food intake, and concomitant weight loss in half of the mice in the experimental group. The failure of the other half to respond is not presently understood. However, 100 percent of mice administered pokeweed mitogen systemically exhibited anorexia and experienced a statistically significant drop in circulating blood glucose levels and body weight. Thus, in circumstances wherein there is no response to oral lectin administration, the lectin should be administered systemically instead via intravenous, parenteral, subcutaneous, transdermal or intramuscular dosage methods.

The following examples further illustrate the present invention, and are not to be construed as limiting the scope thereof. All parts and percentages are by weight unless expressly indicated to be otherwise.

EXAMPLES

The effect of lectins on circulating blood glucose levels and body weight can be determined using standard techniques according to the following test protocol.

Materials and Methods

Animals: Male BALB/c, C57BL/6, ob/ob and CB6 F1 (C57BL/6×BALB/c) (from Jackson Labs, Inc., Bar Harbor, Me.) or BALB/c SCID (severe combined immune deficiency, from Taconic Farms, Germantown, N.Y.) mice were housed in a 12/12 light/dark cycle with standard laboratory chow (Purina Mills, Inc., Il.) and water ad lib for at least two days before use.

CB6 mice were made diabetic by injecting streptozotocin (200 mg/kg i.p. in PBS) one time and measuring blood glucose four days later. At this time, the mice given streptozotocin had serum glucose concentrations of 420±10 mg/dl, twice normal values.

Blood was collected by retro-orbital bleeding to determine diabetic state prior to receiving pokeweed mitogen and to measure TNFα and Ill.-6 concentrations one and three hours, respectively, after pokeweed mitogen treatment in the corresponding studies. For other measurements, blood, by cardiac puncture, and tissue samples were collected after sacrifice by cervical dislocation.

Reagents: Pokeweed mitogen (PKW), Momordica lectin, streptozotocin and Triton X-100 were purchased from Sigma Chemical Co. (St. Louis, Mo.) and chloroform from J.T. Baker, Inc. (Phillipsburg, N.J.). Serum glucose was measured using a commercial kit (Sigma), and insulin concentrations were determined using a radioimmunoassay kit (ICN, Costa Mesa, Calif.). The BCA protein assay was purchased from Pierce (Rockford, Ill.). IL-6 and TNF-α were measured using enzyme-linked immunosorbant assays (R&D Systems, Minneapolis, MN and Biosource International, Inc., Camarillo, Calif., respectively). The TNF-α antagonist (TNFbp) was the kind gift of Amgen Boulder, Inc. (Boulder, Colo.). TNFbp consists of the extracellular domains of two type 1 (p55) TNFα receptors linked to polyethylene glycol. The anti-IL'6 antibody (20F3) was grown in nude mice from hybridoma cells and purified using standard antibody isolation procedures (Pierce, Rockford, Ill.). For the glucose uptake study, 2-deoxy-D-[1-$^3$H]glucose was purchased from Amersham Life Science (Elk Grove, Ill.). Dulbecco's modified eagle medium, RPMI and fetal bovine serum were purchased from JRH Biosciences (Lenexa, Kans.). Horse serum was purchased from Sigma. For T and B lymphocyte isolation, the Ficoll was from Sigma, the magnetic beads were from Dynal (Lake Success, N.Y.), the antibodies were from Becton-Dickinson (Mountain View, Calif.). The $^3$H-thymidine was from New England Nuclear (Boston, Ma).

Treatments: Pokeweed mitogen was dissolved in sterile PBS and given by intra peritoneal injection (i.p.), or orally, by gavage, in a volume of 200 μl/20 g mouse. For dosages of 15 mg/kg, 300 μg PKW was dissolved in 200 μl water. For 10 mg/kg and 5 mg/kg dosages, the level of PKW was reduced proportionately. TNFbp and anti-IL-6 were given i.p. two hours prior to PKW in the studies described. The TNFbp dose was 780 μg/mouse in 100 μl of vehicle. The quantity of TNF-A antagonist given was 35-fold greater than a dose which protected against death in the D-galactosamine/LPS model of liver injury disclosed by Russell et al., *J.Infect. Dis.*, 171, 1578-83 (1995). The dosage of anti-IL-6 (20F3) was 650 μg/mouse, in a 150 μl volume. Control animals received the same vehicle and volume at the appropriate time.

Chloroform extraction of pokeweed mitogen: The PKW solution used to treat mice was mixed thoroughly with an equal volume of chloroform by vortexing at moderate speed for 30 minutes. A precipitate appeared in the chloroform layer which was separated by centrifugation. Both the clear chloroform layer and the precipitate were dried under nitrogen at room temperature and then under vacuum to remove the chloroform. These extracts were redissolved in the same volume of the original vehicle (PBS). Mice were treated i.p. with the extracted pokeweed solution or with the reconstituted extracts in the subsequent study reported below.

The chloroform layer contained no protein, while the precipitate contained 14 percent as much protein as the unextracted PKW solution. The protein content of the aqueous layer plus the precipitate was equal to the protein content of the unextracted solution.

Human B and T lymphocyte stimulation by chloroform-treated pokeweed mitogen: B cells and T lymphocytes were purified from heparinized human blood by separating PBMC over a Ficoll gradient, followed by passage over a nylon wool column. Adherent cells were depleted of non-B lymphocytes by using dynal magnetic beads either directly conjugated with anti-CD4 and anti-CD8 antibody, orby adding anti-CD16 or -CD14 antibody to the cells and following this with anti-mouse IgG or IgM-coated beads in a secondary step. The B lymphocytes were plated as $1 \times 10^5$ cells/well and the T lymphocytes were plated as $2 \times 10^5$ cells/well on a 96 well plate. The three pokeweed mitogen fractions—unextracted, extracted and chloroform precipitate—were added and, two days later, 0.5 μCi $^3$H-thymidine was added to each well. At the end of eight hours, thymidine uptake into the cells was measured.

Ex vivo exposure of blood to pokeweed mitogen: 75 μg of the pokeweed mitogen mixture in a volume of 50 μg was added to 0.5 mL of heparinized blood. This is equal to the contribution that the PKW solution used for acute mouse studies would give to 2 mL of blood, roughly the blood content of a 20 g mouse. The treated blood was incubated for six hours at 38° C. in 5 percent $CO_2$. Blood was removed at intervals, plasma was separated and glucose was measured.

Deoxyglucose uptake in vitro: Murine-derived C2C12 myoblast cells were obtained from the American Type Culture Collection (Rockville, Md.). These cells were plated in 24 well plates and grown in high glucose DMEM containing 10 percent fetal bovine serum. At confluence, the medium was replaced with high glucose RPMI containing 10 percent horse serum. Four days later, myotubes were formed, and the medium was replaced with low glucose DMEM+2 percent FBS containing the treatments. Sixteen hours later, 0.2 μCi 2-deoxy-D-[1-$^3$H]glucose/well was added for 20 minutes. Afterwards, the cells were washed three times with PBS, solubilized in 1 percent Triton X-100 and radioactivity and protein concentrations were measured.

Statistics: In all groups, n=3-10. The data are presented as mean±SEM. Groups were compared using the two tailed paired or unpaired t-test or two-way ANOVA, followed by the post hoc Fisher's test, as appropriate. When comparing body weights, except where noted (Table I, study II), all groups which were statistically different from the control group at the time of sampling also differed significantly when compared to their initial (pretreatment) body weights.

RESULTS

Figure 1A:
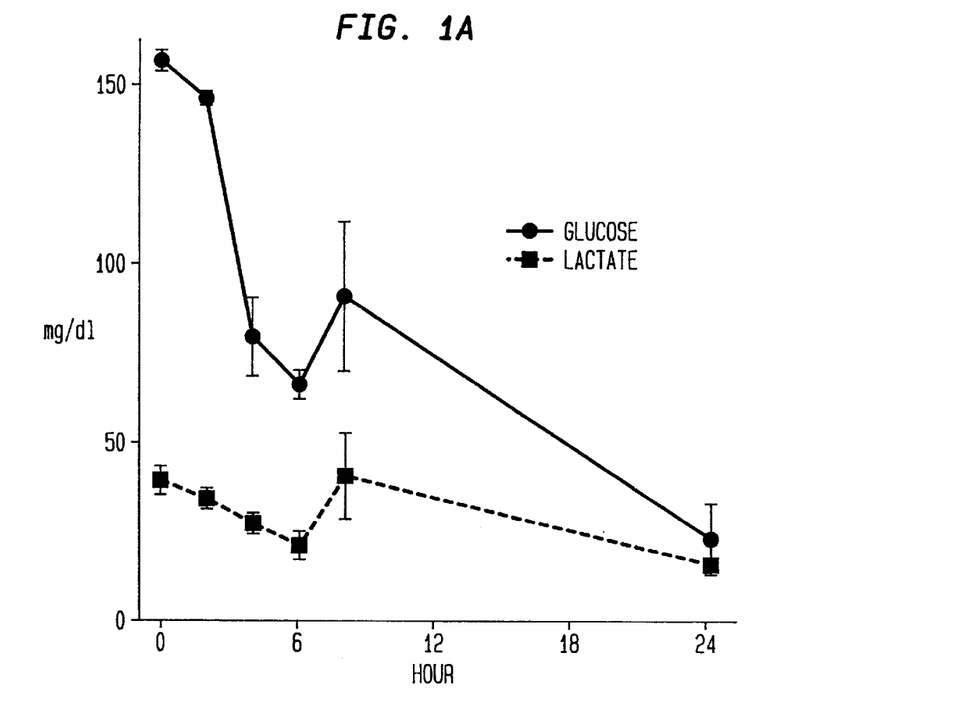

Circulating glucose concentrations: Glucose concentrations in the vehicle-treated control group were 154±3 mg/dl. Mice given 15 mg/kg PKW showed a significant hypoglycemia by four hours, declining to 78±11 mg/dl, p<0.05 vs. controls. These concentrations declined further, to 23±10 mg/dl at 24 hours (FIG. 1*a*). Blood lactate concentrations changed in parallel with glucose, being 39±4 mg/dl in PBS-treated animals, 27±4 mg/dl four hours later and 16±2 mg/dl at 24 hours.

Figure 1B:
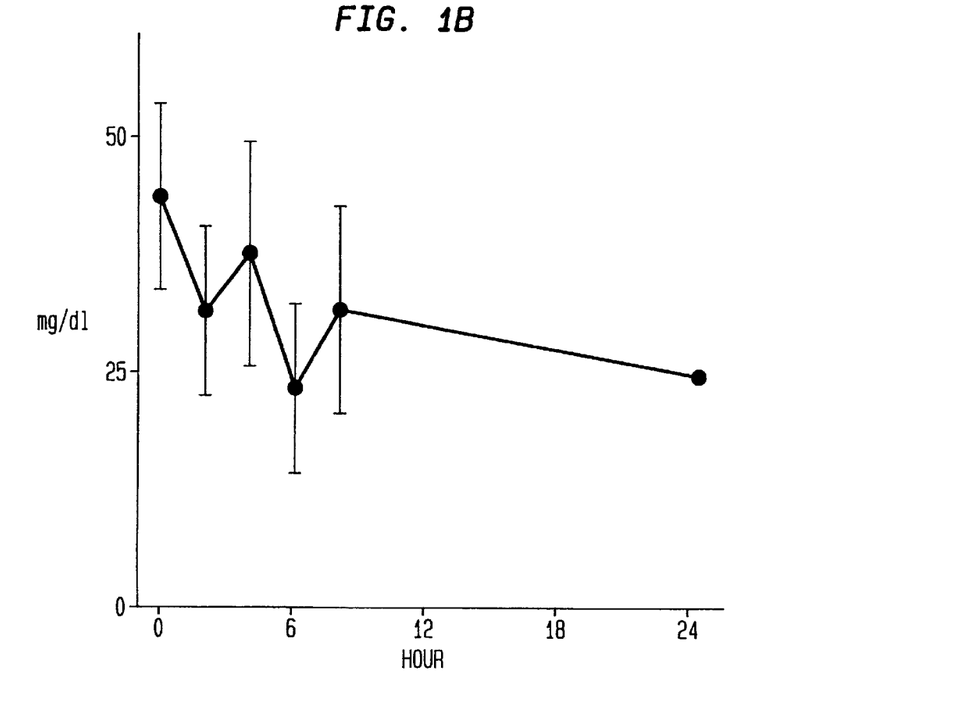

The hypoglycemia that followed PKW administration was not secondary to stimulated insulin release. Plasma insulin concentrations decreased after receiving PKW, from 43±10 μU/mL to 24±0 μU/mL 24 hours later, p<0.05 (FIG. 1*b*), while diabetic mice given PKW had a circulating glucose 45 percent lower than the diabetic control group, also p<0.05 (Table I). A decline in food intake did not contribute significantly to the lowered glucose levels in mice given PKW (Table I).

The effects of pokeweed mitogen were induced by oral administration (by gavage) in 50 percent of the animals that received it. The non-responders had blood glucose of 210±17 mg/dl, while the responders had blood glucose of 70±5 mg/dl and significantly lower body weights (Table I).

TABLE I

Circulating Glucose, Food Intake and Weight Loss Induced By Various Treatments in Normal, SCID, and Siabetic Mice

| | Treatment | Glucose, mg/dl | Food Intake, g/mouse | Body Weight, g |
|---|---|---|---|---|
| I. | vehicle | 248 ± 13 | 3.26 | 17.5 ± 0.3 |
| | PKW only | 34 ± 7* | 0.07 | 17.0 ± 0.3 |
| | PKW + anti-IL-6 body | 81 ± 22*◊ | 0.22 | 17.7 ± 0.3 |
| | PKW + TNFbp | 112 ± 19*◊ | 0.93 | 17.3 ± 0.4 |
| | PKW + anti-IL-6 + TNFbp | 120 ± 14*◊ | 0.16 | 18.5 ± 0.5 |
| II. | vehicle | 191 ± 6 | 3.55 | 18.8 ± 0.2 |
| | PKW | 74 ± 12* | 0 | 16.3 ± 0.6* |
| | chloroform-extracted PKW | 144 ± 19 | 0.38 | 16.2 ± 0.3* |
| | chloroform extract | 265 ± 24* | 2.63 | 17.1 ± 0.7 |
| | chloroform precipitate | 106 ± 14* | 0 | 16.0 ± 0.2* |
| III. | SCID + vehicle | 126 ± 8 | 2.85 | —▽ |
| | SCID + PKW | 77 ± 8* | 0.60 | — |
| IV. | diabetes + vehicle | 421 ± 14 | — | 16.0 ± 0.3 |
| | diabetes + PKW | 227 ± 40* | — | 13.2 ± 0.8* |
| V. | vehicle | 205 ± 17 | — | — |
| | PKW | 96 ± 5* | — | — |
| | fasting | 192 ± 12 | — | — |
| VI. | oral, non-responder | 210 ± 17 | — | 18.6 ± 0.2 |
| | oral responder | 70 ± 5* | — | 16.5 ± 0.2* |

*p < .05 vs. control group in respective study.
◊p < .05 vs. respective PKW-treated group.
♦NS vs. initial body weight.
▽not done.

Figure 2A:
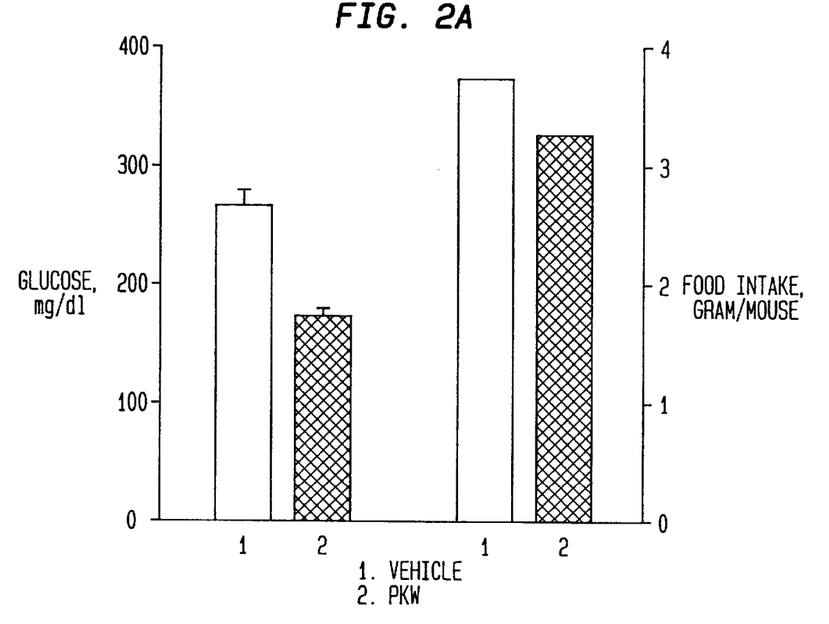
Figure 2B:
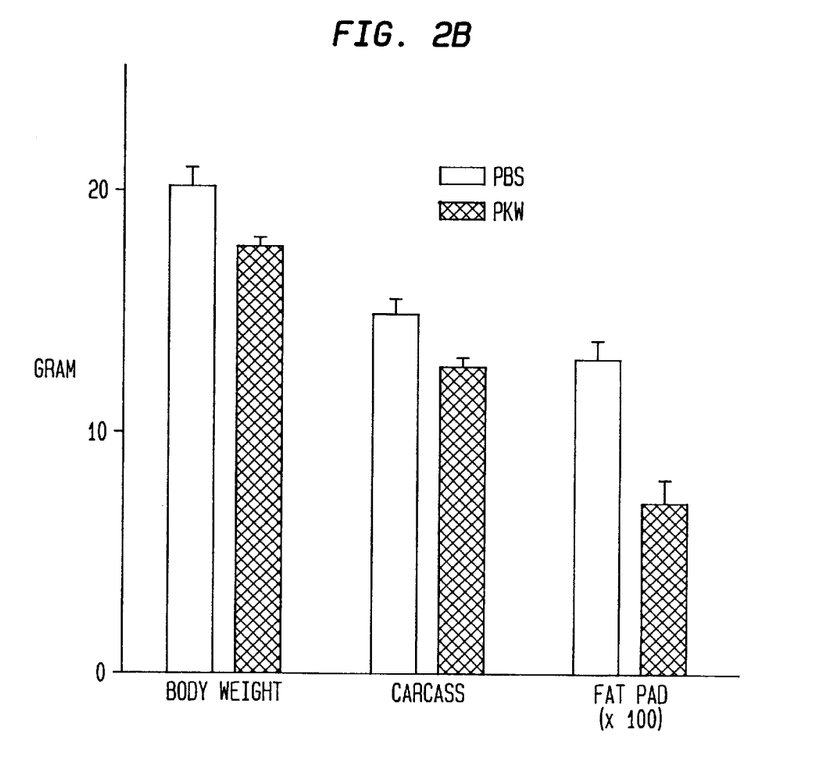

Body composition and food intake. A single treatment of 15 mg/kg PKW had effects lasting for three days (FIG. 2a). The decline in body weight at this time was due to the loss of both lean tissue and adipose tissue. Lean tissue, represented by carcass weight, was 14.9±0.4 g in the control group and 12.8±0.4 g in the PKW-treated group, p<0.05. The adipose tissue, represented by the epididymal fat pad, was 0.12±0.01 g in the control group and 0.07±0.01 g in the PKW-treated group, p<0.05. These tissue comparisons are illustrated in FIG. 2b.

Chronic treatment with PKW. When mice were given PKW at a dose of 5 mg/kg i.p. once every two days, body weight and food intake declined dramatically. On day three, after two treatments, three of the five mice were dead.

Figure 3A:
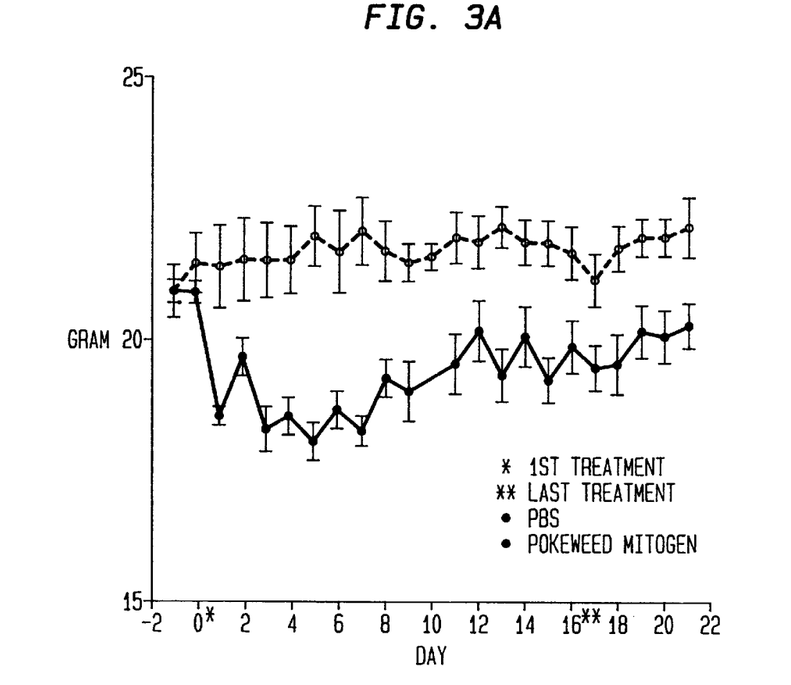
Figure 3B:
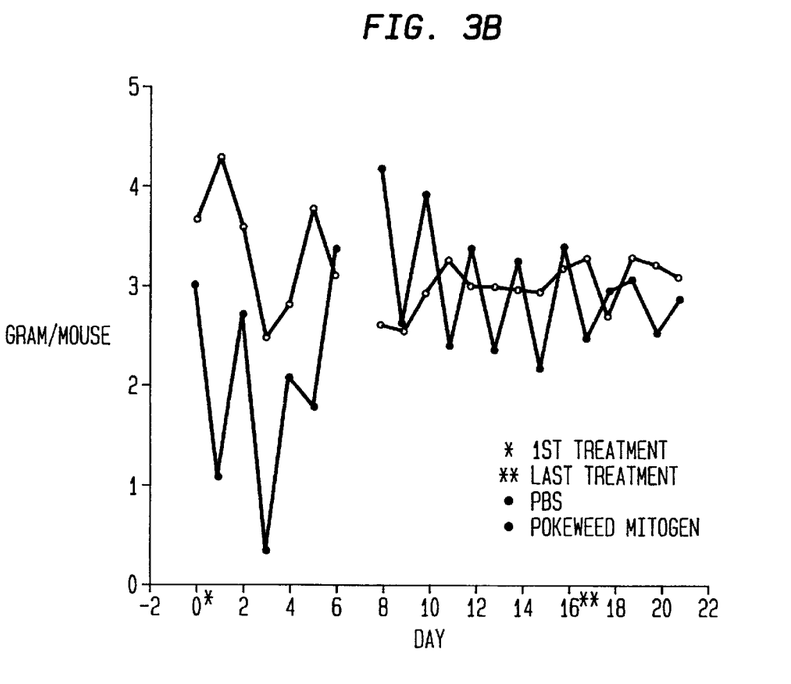

In a second part of this study, illustrated in FIGS. 3a and 3b, mice were given PKW at a lower dose, 3 mg/kg/2 days, for 16 days. Food intake recovered one day after each treatment. Beyond three days, the average food intake was roughly equal to that of the control group, oscillating above and below it in response to PKW. In the treated group, body weight was 21.0±0.2 g at the start, but declined 15 percent, to 17.9±0.4 g by day five (p<0.05 vs. both Day 0 and the control group). The body weight of this group increased after day five, but remained below that of the control group for the additional ten days of treatment and for one week of monitoring after the treatment was discontinued.

Immune mediation of hypoglycemia: Circulating TNFα did not increase after a 15 mg/kg dose of PKW was given. However, an elevation in the circulating concentration of IL-6, to 129±6 ng/mL, was found, compared to undetectable levels in control animals (Table II). Pretreatment with TNFbp attenuated the IL-6 appearance 32 percent. The blood glucose concentration was significantly higher in mice given PKW+TNFbp, as was food intake. Despite an effect, both these indices remained low (Table I).

Mice given anti-IL-6 antibody prior to 15 mg/kg i.p. PKW did not present with a decline in circulating JL-6 concentrations (Table II). Although TL-6 concentrations appeared unaffected, the anti-IL-6 attenuated hypoglycemia to an extent which was equivalent to the effect of TNFbp, but anorexia was unaffected, shown in Table I. The cytokine antagonists were not additive in their protective effects. All of the groups in this specific study lost weight overnight, possibly due to the stress of being given two i.p. injections and eyebled in the span of three or five hours.

SCID mice, which do not have functional T or B lymphocytes and cannot mount an allergic reaction, were not less sensitive to the hypoglycemia effect of PKW (Table I). These immunodeficient mice also responded with the appearance of circulating IL-6, to 92±35 ng/mL in the treated animals (Table II).

TABLE II

Cytokine Appearance After PKW Administration

| | Normal | TNFα pg/mL | IL-6, ng/mL |
|---|---|---|---|
| I. | vehicle | not detectable | not detectable |
| | PKW only | not detectable | 129 ± 6* |
| | PKW + anti-IL-6 antibody | —◊ | 123 ± 22* |
| | PKW + TNFbp | not detectable | 40 ± 5* |
| | PKW + anti-IL-6 + TNFbp | — | 104 ± 5* |
| II. | SCID | | |
| | vehicle | — | not detectable |
| | PKW | — | 92 ± 35* |

*p < .05 vs. control group in respective study.
◊ not done.

Chloroform extraction of pokeweed mitogen: Data from this study are presented in Table I. The vehicle-treated group had circulating glucose concentrations of 19±16 mg/dl, while in the PKW-treated group, glucose levels were 74±12 mg/dl, p<0.05. The same solution of pokeweed mitogen was mixed with chloroform, the results described below.

The aqueous chloroform-extracted PKW solution had only a mild hypoglycemia effect, to 144±19 mg/dl, NS. Food intake declined, but body weight did not.

The chloroform precipitate induced a significant hypoglycemia (106±14 mg/dl), weight loss and complete anorexia. This was in spite of a lower protein content in the reconstituted precipitate solution, constituting a dosage of 2.1 mg protein/kg, rather than 15 mg/kg.

The chloroform extract, which did not contain any protein, had no effect on body weight or food intake. With this preparation, the circulating glucose concentrations increased to 265±24 mg/dl, p<0.05 vs. controls.

Human B cell and T lymphocyte stimulation by pokeweed mitogens: Unstimulated thymidine uptake by B lymphocytes was 241±4 cpm/well. At 5 $\mu$g/mL, the chloroform precipitate increased thymidine uptake by B cells to 2633±267 cpm/well, 40 percent greater than unextracted PKW and 265 percent greater than the chloroform-extracted solution of PKW. Regarding T lymphocytes, baseline thymidine uptake was 750±46 cpm/well. The extracted PKW caused the greatest thymidine uptake, to 42213±762 cpm/ well. This was 24 percent greater than the PKW solution and 39 percent greater than the chloroform precipitate (Table IV).

Ex vivo exposure of blood to pokeweed mitogen: Incubating mouse blood with PKW had no effect on the rate of glucose disappearance in the blood (Table III).

TABLE III

Blood Glucose Concentrations After Vehicle Or Pokeweed Mitogen Administration For Various Incubation Periods

| Hour | Vehicle | Pokeweed Mitogen |
|------|---------|------------------|
| 0 | 206 ± 7 | 196 ± 12 |
| 1 | 142 ± 10 | 142 ± 9 |
| 2 | 111 ± 10 | 111 ± 9 |
| 3 | 92 ± 8 | 87 ± 4 |
| 6 | 9 ± 7 | 7 ± 4 |

Glucose concentrations are mg/dl of plasma. PKW was added at a level of 150 µg/mL of blood.

TABLE IV

B Lymphocyte And T Lymphocyte Stimulation Of By Pokeweed Mitogen And Chloroform Fractions Of Pokeweed Mitogen

| | B Lymphocyte | T Lymphocyte |
|---|---|---|
| vehicle | 241 ± 4 | 750 ± 46 |
| pokeweed mitogen | 1876 ± 291* | 36696 ± 1001 |
| chloroform extracted PKW | 720 ± 10 | 42243 ± 767* |
| chloroform precipitate | 2633 ± 267* | 33359 ± 1457 |

*$p < .05$ vs. vehicle and chloroform extracted PKW

The protein administration was 5 µg/mL for all treated groups, incubations for three days. Exposure to 0.5 µCi $^3$H-thymidine was for eight hours. Measurements represent cellular $^3$H-thymidine uptake as cpm/well.

Deoxyglucose uptake by C2C12 myotubes: The baseline glucose uptake in these cells was 63±7 cpm/mg cellular protein. An insulin concentration of 1 µM stimulated a 48 percent increase in deoxyglucose uptake, while 10 µg/mL of the chloroform precipitate fraction of PKW stimulated deoxyglucose uptake a similar amount, to 93±12 cpm/mg protein (both $p<0.05$). The stimulation of deoxyglucose uptake by the chloroform precipitate fraction of PKW was confirmed in a second study comparing the PKW fractions, shown in Table V.

$^3$H-deoxyglucose Uptake by C2C12 Myotubes Incubated With Fractions of Pokeweed Mitogen

| | cpm/mg Cellular Protein |
|---|---|
| vehicle | 44.3 ± 3.9 |
| chloroform preciptate | 61.3 ± 4.9* |
| chloroform-extracted pokeweed mitogen | 54.9 ± 5.9 |
| pokeweed mitogen | 44.2 ± 3.8 |

*$p < .05$ vs. vehicle

20 µl of PBS or the treatment solutions were added to each well, yielding 4 µg/mL of the precipitate, 26 µg/mL of the extracted solution and 30µg/mL of the pokeweed mitogen solution used to derive the other treatments. The myotubes were incubated with the treatments for 18 hours prior to $^3$H-deoxyglucose exposure. Incubation with 0.2 µCi $^3$H-deoxyglucose was for 20 minutes; and n=8–12 wells/group.

Treatment of obese mice with PKW: When obese ob/ob mice were given a single PKW dose (10 mg/kg i.p.), serum glucose levels and food intake declined dramatically. On day two, half of one group of mice died, likely due to starvation. This is attributed to their abnormal metabolism. Apparently obese ob/ob mice are more sensitive to PKW. The remaining group, n=4, was used for the data depicted in Table 6. The mice were given the PKW and blood was collected just prior to administration by retro-orbital bleeding and 18 hours later by cardiac puncture.

TABLE VI

| ob/ob Mice | Food Intake, g/Mouse | Serum Glucose | wt. Loss |
|---|---|---|---|
| before pokeweed mitogen | 4.1 | 424 ± 4 | |
| after 10 mg/kg | 0.0 | 55 ± 8 | 2% |

This demonstrates that the obese ob/ob mouse, used as a model of obesity, is sensitive to PKW. Although the mice did not lose as much weight as normal mice, this was expected on the basis of their documented lower metabolism and higher body fat content, i.e., the lost fat weighs less than protein or carbohydrate loss because of the water associated with the latter two body compartments.

Acute treatment with Momordica lectin: When mice were given a single Momordica lectin dose (15 mg/kg i.p.), circulating blood glucose levels, body weight and food intake also declined dramatically, to a degree equivalent to that experienced with PKW. The results are depicted in Table VII:

TABLE VII

Effects Of Different Lectins On Circulating Glucose And Body Weight In Mice

| Treatment | Body Weight, g Day 0 | Day 1 | Weight Change | Food Eaten g/ Mouse | Glucose mg/dl |
|---|---|---|---|---|---|
| vehicle | 22.2 ± 1.0 | 22.5 ± 0.9 | 0.3 ± 0.2 | 1.56 | 223 ± 12 |
| pokeweed | 22.7 ± 0.6 | 20.7 ± 0.6 | −1.9 ± 0.1 | 0.16 | 81 ± 7 |
| Momordica | 22.4 ± 0.6 | 20.4 ± 0.2 | −2.0 ± 0.5 | 0.20 | 124 ± 13 |

Pokeweed and Momordica lectins appear to have insulin-like activity in mice, and induce hypoglycemia and weight loss in these animals, even when given orally. Such orally active proteins can be used in the treatment of insulin-dependent diabetes mellitus or obesity, offering a new therapeutic strategy for treating these diseases.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A method of inducing weight loss in a mammal in need thereof comprising administering to said mammal a lectin selected from the group consisting of a pokeweed mitogen chloroform precipitatable fraction and Momordica lectin in an amount between about 1 and about 100 micrograms per kilogram of body weight per day that is effective to induce a decline in food intake in said mammal and continuing said administering step to maintain the decline in food intake.

2. The method of claim 1, wherein said lectin consists essentially of said pokeweed mitogen chloroform precipitatable fraction.

3. The method of claim 2, wherein said repeating step comprises repeating said administering step daily until said decline in food intake produces a weight loss of at least about 10 percent.

4. The method of claim 3, wherein said method further includes the step of administering said lectin in a reduced amount or with reduced frequency after said weight loss of at least about 10 percent is obtained.

5. The method of claim 1, wherein said administering step comprises administering said lectin orally.

6. The method of claim 1, wherein said administering step comprises administering said lectin systemically.

7. The method of claim 1, wherein said administering step comprises administering said lectin to said mammal in an amount effective to induce a decline in food intake without inducing hypoglycemia.

8. A method of treating adult-onset diabetes in a mammal in need thereof comprising administering to said mammal a pokeweed mitogen chloroform precipitatable fraction in an amount between about 1 and about 100 micrograms per kilogram of body weight per day that is effective to induce hypoglycemia in said mammal.

9. The method of claim 8, wherein said method further includes the step of continuing said administering step to maintain the decline in food intake and hypoglycemia state.

10. The method of claim 9, wherein said continuing step comprises repeating said administering step daily.

11. The method of claim 10, wherein said repeating step comprises repeating said administering step daily until a blood glucose level less than about 150 mg/dl is obtained.

12. The method of claim 11, further including the step of administering said lectin in a reduced amount or with reduced frequency after a blood glucose level less than about 150 mg/dl is obtained.

13. The method of claim 10, wherein said lectin is administered in an amount effective to induce a decline in food intake.

14. The method of claim 13, wherein said repeating step comprises repeating said administering step daily until said decline in food intake produces a weight loss of at least about 10 percent.

15. The method of claim 14, further including the step of administering said lectin in a reduced amount or with reduced frequency after said weight loss of at least about 10 percent is obtained.

16. The method of claim 8, wherein said administering step comprises administering said lectin orally.

17. The method of claim 8, wherein said administering step comprises administering said lectin systemically.

18. A method of treating adult-onset diabetes in a mammal in need thereof comprising administering to said mammal a dosage consisting essentially of Momordica lectin in an amount effective to induce a decline in food intake and induce hypoglycemia in said mammal, and repeating said administering step daily until said decline in food intake produces a weight loss of at least about ten percent.

19. The method of claim 18, wherein said administering step comprises administering between about 1 and about 100 micrograms of said lectin per kilogram of body weight per day.

20. A method of treating adult-onset diabetes in a mammal in need thereof comprising administering to said mammal a dosage form consisting essentially of Momordica lectin in an amount effective to induce hypoglycemia in said mammal.

21. The method of claim 20, wherein said administering step comprises administering between about 1 and about 100 micrograms of lectin per kilogram of body weight per day.

22. The method of claim 20, wherein said lectin is administered in an amount effective to induce a decline in food intake.

23. The method of claim 22, wherein said administering step comprises administering said lectin daily until said decline in food intake produces a weight loss of at least about 10 percent.

* * * * *